United States Patent
Brezinski et al.

(10) Patent No.: US 12,262,989 B2
(45) Date of Patent: Apr. 1, 2025

(54) TISSUE COLOR MEASUREMENT DEVICE

(71) Applicant: LITTLE SPARROWS TECHNOLOGIES INC., Winchester, MA (US)

(72) Inventors: Donna Jean Brezinski, Winchester, MA (US); Nolan Todd Smith, Newburyport, MA (US); Gary Eugene Gilbert, Winchester, MA (US)

(73) Assignee: LITTLE SPARROWS TECHNOLOGIES, INC., Winchester, MA (US)

( * ) Notice: Subject to any disclaimer, the term of this patent is extended or adjusted under 35 U.S.C. 154(b) by 0 days.

(21) Appl. No.: 18/271,976

(22) PCT Filed: Jan. 13, 2022

(86) PCT No.: PCT/US2022/012302
§ 371 (c)(1),
(2) Date: Jul. 12, 2023

(87) PCT Pub. No.: WO2022/155327
PCT Pub. Date: Jul. 21, 2022

(65) Prior Publication Data
US 2024/0023827 A1 Jan. 25, 2024

Related U.S. Application Data

(60) Provisional application No. 63/137,294, filed on Jan. 14, 2021.

(51) Int. Cl.
*A61B 5/103* (2006.01)
*A61B 5/00* (2006.01)

(52) U.S. Cl.
CPC ............ *A61B 5/1034* (2013.01); *A61B 5/441* (2013.01)

(58) Field of Classification Search
CPC .................. A61B 5/1034; A61B 5/441; A61B 2560/0242; G01N 21/293
See application file for complete search history.

(56) References Cited

U.S. PATENT DOCUMENTS 5,009,507 A * 4/1991 Katz .................... G01N 21/293
356/421
6,437,863 B1 8/2002 MacFarlane et al.
(Continued)

FOREIGN PATENT DOCUMENTS

KR 100374807 B1 * 5/2003 ................ G01J 3/46

OTHER PUBLICATIONS

Gosset, "A Perspex Icterometer for Neonates", The Lancet, Jan. 9, 1960, pp. 87-88 (Year: 1960).*
(Continued)

*Primary Examiner* — Jacqueline Cheng
*Assistant Examiner* — Tho Q Tran
(74) *Attorney, Agent, or Firm* — Nixon Peabody LLP; Ronald I. Eisenstein; Ravinderjit S. Braich (57) ABSTRACT

The disclosure provides a device for measuring serum bilirubin levels and uses thereof. The device includes a plate including a surface comprising: a stepwise gradient of colors; a lighting indicator; and a series of windows in the surface, each window in the series bordered by one of the colors, and each window including a transparent portion in the plate.

20 Claims, 5 Drawing Sheets

(56) References Cited

U.S. PATENT DOCUMENTS

| | | | |
|---|---|---|---|
| 6,452,188 B1* | 9/2002 | Chubb | A61B 5/1034 |
| | | | 250/461.2 |
| 2003/0031872 A1* | 2/2003 | Arps | A61L 29/16 |
| | | | 428/408 |
| 2019/0110716 A1* | 4/2019 | Sunwoo | A61B 3/10 |
| 2019/0328915 A1* | 10/2019 | Paul | A61L 2/085 |
| 2020/0211693 A1 | 7/2020 | Adiri et al. | |

OTHER PUBLICATIONS

Healey et al. (Blog Post for the Tayside Medical History Museum) (Year: 2023).*

Lee et al. "A Novel Icterometer for Hyperbilirubinemia Screening in Low-Resource Settings." Pediatrics 143.5 (2019).

Zandi et al. "Optimising metameric spectra for integrative lighting to modulate the circadian system without affecting visual appearance." Scientific reports 11.1 (2021): 23188.

Ugra, "Ugra Light Indicator Strip D50—Ugra," Retrieved from the internet at <https://web.archive.org/web/20201021153831/https://www.ugra.ch/en/product/ugra-light-indicator-strip-d50/> Oct. 21, 2020 (4 Pages).

Williams et al. "The 'Gosset' Icterometer: a brief history." West of England Medical Journal 115.4.3: 1-4, Retrieved from the Internet at <https://www.northamptongeneral.nhs.uk/About/OurHistory/Dr-Gosset/The-Gosset-Icterometer.aspx#ad-image-0> (2016).

* cited by examiner

TISSUE COLOR MEASUREMENT DEVICE

CROSS-REFERENCE TO RELATED APPLICATIONS

This application is a 35 U.S.C. § 371 National Phase Entry Application of International Application No. PCT/US2022/012302, filed Jan. 14, 2022, which claims benefit under 35 U.S.C. § 119 (e) of U.S. provisional application No. 63/137,294 filed Jan. 14, 2021, the contents of both of which are incorporated herein by reference in their entirety.

FIELD OF THE INVENTION

This invention relates to a device for measuring the tissue color in a subject. More particularly, the invention is directed to the measurement of bilirubin in a subject.

BACKGROUND

Severe neonatal jaundice or "hyperbilirubinemia" (serum bilirubin equal to or greater than 20 mg/dL) affects ~1 million newborns annually and places them at risk for permanent brain injury or death. It is critical to monitor newborns for elevated bilirubin so that therapeutic intervention can occur before serum levels become high. The "gold standard" for measurement of bilirubin is serum measurements from blood. These require a heel puncture or venapuncture to obtain a blood sample which is painful to infants and distressing to caregivers.

An early icterometer, the 'Gosset' icterometer, provided a non-invasive device having stripes of graded yellow color shades painted or adhered on a transparent plastic with gaps between them [A. N. Williams et al., *West of England Medical Journal;* 115 (4), Article 3, Dec. 2016, pg. 1-4]. In the areas of the transparent gaps the plastic device is pressed against the skin, such as the nose, of an infant to temporarily blanch the skin and reveal the underlying subcutaneous tissue color. Matching of the yellow color stripes to subcutaneous tissue color, and reference to an associated chart of bilirubin ranges that corresponded to each color provided an estimate of the level of bilirubin. Although the device was economical, its adoption for detection of jaundice was short lived due to difficulties in use. In particular, interpretation of color-matching between skin and color stripes was sensitive to the lighting environment and users reported unreliable results due to poor lighting [B. Wood, The icterometer, *Pediatrics* (1962); 30(4): Pg. 664-665]. In addition, the device was not easy to clean since the colors were attached or painted on exposed surfaces, and, although not invasive, the device did require physical contact with the infant.

Improved devices that provide accuracy and are not invasive use spectrophotometric methods for jaundice assessment [K. A. Jangaard et al., *Paediatr Child Health;* 11(2) February 2006, Pg. 79-83]. However, such devices are expensive and require a power source. This presents a barrier to implementation when jaundiced babies are evaluated where such equipment is typically not available such as in downstream healthcare settings such as primary healthcare clinics or the home, and where resources are scarce such as in developing countries.

A recent improved device includes an icterometer similar to the Gosset icterometer but with holes punched through the colored areas providing a clear window through which blanched skin is viewed. This provides an easier comparison of the colored areas to the blanched skin color. The device is low cost and noninvasive. If used under proper lighting the device provides high diagnostic accuracy for neonatal jaundice screening [Anne C. C. Lee, *Pediatrics* 143(5) May 2019, pg. 1-11]. However, the device is still prone to user error as it requires judgement on the part of the user in determining the proper lighting. In addition, the device construction includes punching a hole through the colored areas which are on paper overlayed on, rather than embedded within, a plastic substrate. This constitutes a potential contamination site which limits re-using the device or cleaning it before use.

Therefore, a bilirubin measurement device for improved jaundice screening is still needed. Improvements sought include devices that are economical, cleanable, and easy to use. The present disclosure is directed to solving these and other problems.

SUMMARY

In general, the inventions described herein relate to devices for measurement of bilirubin. The devices are economical and robust, do not require external power and are simple to use. Testing for bilirubin is also non-invasive to the subject, not requiring heel puncture or venapuncture.

A first implementation of the disclosure is an icterometer. The icterometer includes a plate including a surface comprising: a stepwise gradient of yellow colors; a series of windows in the surface, each window in the series bordered by one of the colors, and each window including a transparent portion in the plate; and a lighting indicator configured to indicate the quality of lighting. Optionally, the icterometer further comprises a corresponding color indicium for each color in the color gradient on the surface or on a transparent external surface overlapping the color gradients. Optionally, the lighting indicator is a metameric pair of colored areas on the surface. Optionally, the metameric pair displays metamerism under natural daylight or natural daylight simulators. For example, the metameric pair displays metamerism under D50 or a D65 lighting.

Optionally, the plate is waterproof and inert to cleaning solutions applied to an external surface. Optionally, an external surface of the plate is coated with an antimicrobial coating. Optionally, the plate includes acrylic, polycarbonate, a silica-based glass, or combinations thereof. Optionally, the surface comprising a stepwise gradient of colors is encased in an interior of the plate.

Optionally, the stepwise gradient of colors comprises at least 3 and not more than 10 colors. Optionally, the colors correspond to the colors of subcutaneous tissue of a subject having a total serum bilirubin between about 1.4 and 18 mg/dL. Optionally, the plate is configured as an elongated flat object having a length between about 10 cm and 40 cm, a width between about 2 cm and 5 cm, and a thickness of between about 1 mm and 5 mm.

Optionally, the plate of the icterometer includes: a back plate including, a lip protruding from a surface of the back plate at an outer edge of the back plate, and a series of transparent protrusions in a center area and protruding in the same direction as the lip; a middle layer including the color gradient, the lighting indicator, and a series of through holes, each through hole bordering each one of the transparent protrusions and defining one of the windows, and wherein a first surface of the lip borders an edge of the middle layer; a cover plate comprising a transparent material for viewing of the color gradient and the lighting indicator, and for viewing through the plate at positions corresponding to the transparent protrusions on the back plate; and wherein a second surface of the lip is coupled to a surface of the cover plate and provides a water proof seal. Optionally, the second surface of the lip comprises an adhesive layer. Optionally, the middle layer comprises a web material and the color gradient and lighting indicator are printed, coated or otherwise attached to the web material.

A second implementation of the disclosure is an icterometer including: a plate including a surface comprising, a stepwise gradient of colors; a series of windows in the surface, each window in the series bordered by one of the colors, and each window including a transparent portion in the plate; and wherein the plate is waterproof and inert to cleaning solutions applied to an external surface. Optionally, an external surface of the plate is coated with an antimicrobial coating. Optionally, the plate includes acrylic, polycarbonate, a silica-based glass, or combinations thereof. Optionally, the surface including a stepwise gradient of colors is encased in an interior of the plate. Optionally, the plate is configured as an elongated flat object having a length between about 10 cm and 40 cm, a width between about 2 cm and 5 cm, and a thickness of between about 1 mm and 5 mm.

Optionally, according to the second implementation, the plate comprises: a back plate including, a lip protruding from a surface of the back plate at an outer edge of the back plate, and a series of transparent protrusions in a center area and protruding in the same direction as the lip; a middle layer including the color gradient, and a series of through holes, each through hole bordering each one of the transparent protrusions and defining one of the windows, and wherein a first surface of the lip borders an edge of the middle layer; a cover plate comprising a transparent material for viewing of the color gradient, and for viewing through the plate at positions corresponding to the transparent protrusions on the back plate; and wherein a second surface of the lip is coupled to a surface of the cover plate and provides a water proof seal. Optionally, the second surface of the lip comprises an adhesive layer. Optionally, the middle layer comprises a web material and the color gradient is printed, coated or otherwise attached to the web material.

A third implementation of the disclosure is an icterometer kit. The kit includes an icterometer according to the first or second implementation. Optionally, the sleeve includes stepwise instruction for operation of the icterometer. Optionally, the sleeve includes a table listing color indicia and a corresponding total serum bilirubin concentration.

A fourth implementation of the disclosure is a method for evaluating total serum bilirubin concentration in a subject including: (a) determining a test location having natural or simulated natural lighting using the lighting indicator of the icterometer according to the first implementation; (b) placing the subject in the test location; (c) pressing a window of the icterometer according to the first implementation against the subject's skin to blanch the skin and reveal a subcutaneous tissue color through the window; (d) comparing the subcutaneous tissue color viewed through the window to the color bordering the window; (e) repeating steps (c) and (d) using one or more additional windows of the icterometer; (f) selecting a color that most closely matches the subcutaneous tissue color of the subject; and (g) determining a bilirubin level from tabulated values of color and corresponding bilirubin concentration. Optionally, the icterometer includes at least a first window and a second window; the subcutaneous tissue color corresponds to a color between a first color indicated through the first window and a second color indicated through the second window; and the corresponding bilirubin level is a selected value between the bilirubin level associated with the color viewed through the first window and the second window.

A fifth implementation of the disclosure is a method for evaluation of total serum bilirubin concentration in a subject comprising: (a) identifying a test location having natural or simulated natural lighting; (b) placing the subject in the test location; (c) pressing a window of the icterometer according to the second implementation against the subject's skin to blanch the skin and reveal a subcutaneous tissue color through the window; (d) comparing the subcutaneous tissue color viewed through the window to the color bordering the window; (e) repeating steps (c) and (d) using one or more additional windows of the icterometer; (f) selecting a color that most closely matches the subcutaneous tissue color of the subject; and (g) determining a bilirubin level from tabulated values of color and corresponding bilirubin concentration. Optionally, the icterometer includes at least a first window and a second window; the subcutaneous tissue color corresponds to a color between a first color indicated through the first window and a second color indicated through the second window; and the corresponding bilirubin level is a selected value between the bilirubin level associated with the color viewed through the first window and the second window.

The above summary is not intended to represent each implementation or every aspect of the present disclosure. Additional features and benefits of the present disclosure are apparent from the detailed description and figures set forth below.

BRIEF DESCRIPTION OF THE FIGURES

The disclosure will be better understood from the following description of exemplary embodiments together with reference to the accompanying drawings.

While the present disclosure is susceptible to various modifications and alternative forms, specific implementations and embodiments thereof have been shown by way of example in the drawings and will herein be described in detail. It should be understood, however, that it is not intended to limit the present disclosure to the particular forms disclosed, but on the contrary, the present disclosure is to cover all modifications, equivalents, and alternatives falling within the spirit and scope of the present disclosure as defined by the appended claims.

DETAILED DESCRIPTION

The present inventions can be embodied in many different forms. Representative embodiments are shown in the drawings and will herein be described in detail. The present disclosure is an example or illustration of the principles of the present disclosure and is not intended to limit the broad aspects of the disclosure to the embodiments illustrated. To that extent, elements, and limitations that are disclosed, for example, in the Abstract, Summary, and Detailed Description sections, but not explicitly set forth in the claims, should not be incorporated into the claims, singly or collectively, by implication, inference, or otherwise. For purposes of the present detailed description, unless specifically disclaimed, the singular includes the plural and vice versa; and the word "including" means "including without limitation." Moreover, words of approximation, such as "about," "almost," "substantially," "approximately," and the like, can be used herein to mean "at," "near," or "nearly at," or "within 3-5% of," or "within acceptable manufacturing tolerances," or any logical combination thereof, for example.

Figure 1:
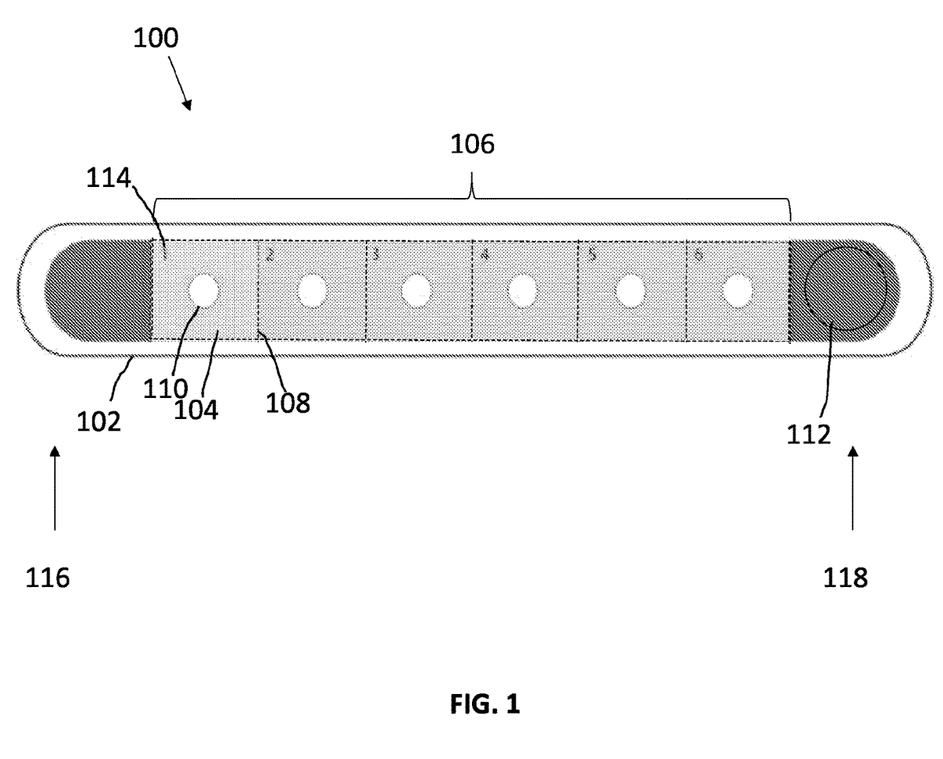
FIG. 1 depicts an icterometer, according to some implementations of the description.

FIG. 1 depicts an icterometer 100, according to some implementations of the description. The icterometer includes a plate 102 including a surface 104. The surface has a step wise gradient of colors 106, each color is shown in FIG. 1 bounded by dashed lines 108 for clarity. As use herein "stepwise" indicates the area in each square indicated by the bounding dashed lines is one color. The plate also includes a series of windows 110, each window in the series is bordered by one of the colors 106. The window is a transparent portion in the plate, allowing visible light to transmit through the plate. In some implementations, the plate also includes a lighting indicator 112 to indicate the quality of the lighting.

In some implementations, the plate further includes a color indicium 114. For example, and without limitation, the indicium can be numbers 1 through 6 shown in FIG. 1. Any other indicia can be used, such as any alphanumeric value, alphanumericals, words, pictograms, etc. In some implementations, each color 106 is assigned a unique indicium. The color indicia 114 can be formed on the surface 104 or any other surface of the plate 102. The color indicia 114 can be formed by any means such as printing, etching, or engraving. In some implementations, the color indicia 114 is positioned on plate 102 so that when it is viewed, it is superimposed on the color 106 that the color indicia 114 is associated with. For example, in some implementations, the color indicia 114 is on the surface 104, while in other implementations the color indicia 114 can be on a transparent cover above surface 104 of plate 102.

The lighting indicator 112 can be any lighting indicator. In some implementations, the lighting indicator 112 is a metameric pair of colored areas on the plate 102. For example, the colored areas can be on the surface 104. The pair of colors are selected to be a metameric pair. That is, the metameric pair appear to be the same color, i.e. displaying "metamerism" under specific lighting conditions. For example, in some implementations, the metameric pair displays metamerism under natural daylight or natural daylight simulators, such as D50 or D65 lighting. Lighting designated D65, or illuminant D65 is a standard artificial daylight illuminant defined by the international commission on Illumination (CIE). Lighting designated D50, or illuminant D50 has a slightly different spectrum.

In some implementations, the icterometer 100 is waterproof and inert to a cleaning solution applied to external surfaces of the plate. As used herein, "inert" refers to the cleaning solution not negatively impacting the use of the icterometer 100. For example, the cleaning solution does not etch, scratch, discolor, and or degrade the structural integrity of the plate 102. As used herein, the cleaning solution can be any solution can be any solution or pure liquid that removes extraneous materials that may adhere to the icterometer 100. For example, extraneous materials can include dirt, grease, bacteria, cells, biological fluids and the like. In some implementations, the cleaning solution includes a disinfectant, bleach, alcohol (e.g., ethanol, isopropanol), a bacteriostat, a detergent, boiling water or combinations of these. In some implementations, the device is inert to boiling water. In some implementations, the device is inert to steam treatment or autoclave conditions. In some implementations, the device is inert to UV light or similar irradiation.

The icterometer 100 can, according to some implementations, be treated with an antimicrobial coating. For example, external surfaces of plate 102 can be treated with an antimicrobial coating. Without limitation, and by way of example, these can include one or more of graphene materials, polycationic hydrogels, silver nanoparticles, polymer brushes, dendrimers, and copper.

The plate 102 can be made using one or more materials. For example, in some implementations, structural materials such as acrylic, polycarbonate and silica-based glass can be used. In particular, optically transparent materials are used to view the colors 106 from the top side of the icterometer 100 (as viewed in FIG. 1) and to form the windows 110. In some implementations, opaque materials can be used, such as along the edges of plate 102, where they do not obscure viewing of colors 106 and windows 110. Opaque materials can include, for example, plastics, rubbers, and metals.

Although FIG. 1 depicts 6 colors 106 and 6 color indicia 114, this is not to be construed as limiting. For example, in some implementations the step wise gradient of colors can be at 3 and not more than 10 colors. Similarly, the optional color indicia can be between 3 and 10, inclusive.

In some implementations, each color 106 is the color associated with the color of subcutaneous tissue. For example, when skin is blanched by compressing it with the device, flow of blood is limited or stopped temporarily, and the underlying color of the fat pad is revealed. This fat pad is where the bilirubin accumulates and can be seen. In some implementations, the colors 106 correspond to the colors of subcutaneous tissue for a subject having total serum bilirubin between about 1.4 and 18 mg/dL.

Although, more colors than 10 can be used in some implementations, this can complicate usage of the icterometer 100 because each color step, or difference between adjacent colors would diminish and be harder for the user to distinguish. In addition, the difference between serum bilirubin levels with more than 10 subdivisions is not critical for screening subjects according to some implementations of this description. Similarly, although in some implementations two colors can be used, this provides limited nuance with respect to bilirubin levels. As used here, bilirubin levels and bilirubin concentrations are used interchangeably.

In some implementations, the plate 102 is configured as a disk, a square or any n-sided object having a diameter greater than its width. In some implementations, the plate 102 is configured as an elongated flat object (e.g., a ruler) having a length between about 10 cm and 40 cm, a width between about 2 cm and 5 cm, and a thickness of between about 1 mm and 5 mm. In some implementations, the plate 102 can include gripping areas near and along edges of the plate, i.e., in areas not obscuring the view of colors 106. For example, although not depicted in FIG. 1, in some implementations, the plate 102 can be dog-bone shaped such that ends 116 and 118 are wider than the area having colors 106. In some implementations, the plate 102 is flat, and in other implementations the plate 102 is curved, such as concave or convex.

In some implementations, the surface 104 which includes the step wise gradient of colors 106 is encased in the plate 102. As used herein, "encased" refers to the surface being surrounded by and protected (e.g., from water and biological fluids) by being an internal surface of the plate 102. In some implementations, the surface 104 is an internal surface upon which the colors 106 are printed or painted upon, and this surface is overlaid with material covering the surface. In some implementations, the surface 104 is a surface on a thin film placed on an internal surface of the plate, and the thin film is overlaid with material covering the thin film. For example, the thin film can be a continuous film such as a plastic or thin metal or the thin film can be a web such as paper.

The icterometer 100 can be made by any method. Without limitation, and by way of example, manufacturing means can include extrusion, casting, molding, additive manufacturing (e.g., 3D printing), subtractive manufacturing (e.g., CNC machining, laser etching), drilling, laser cutting, and combinations of these.

Figure 2:
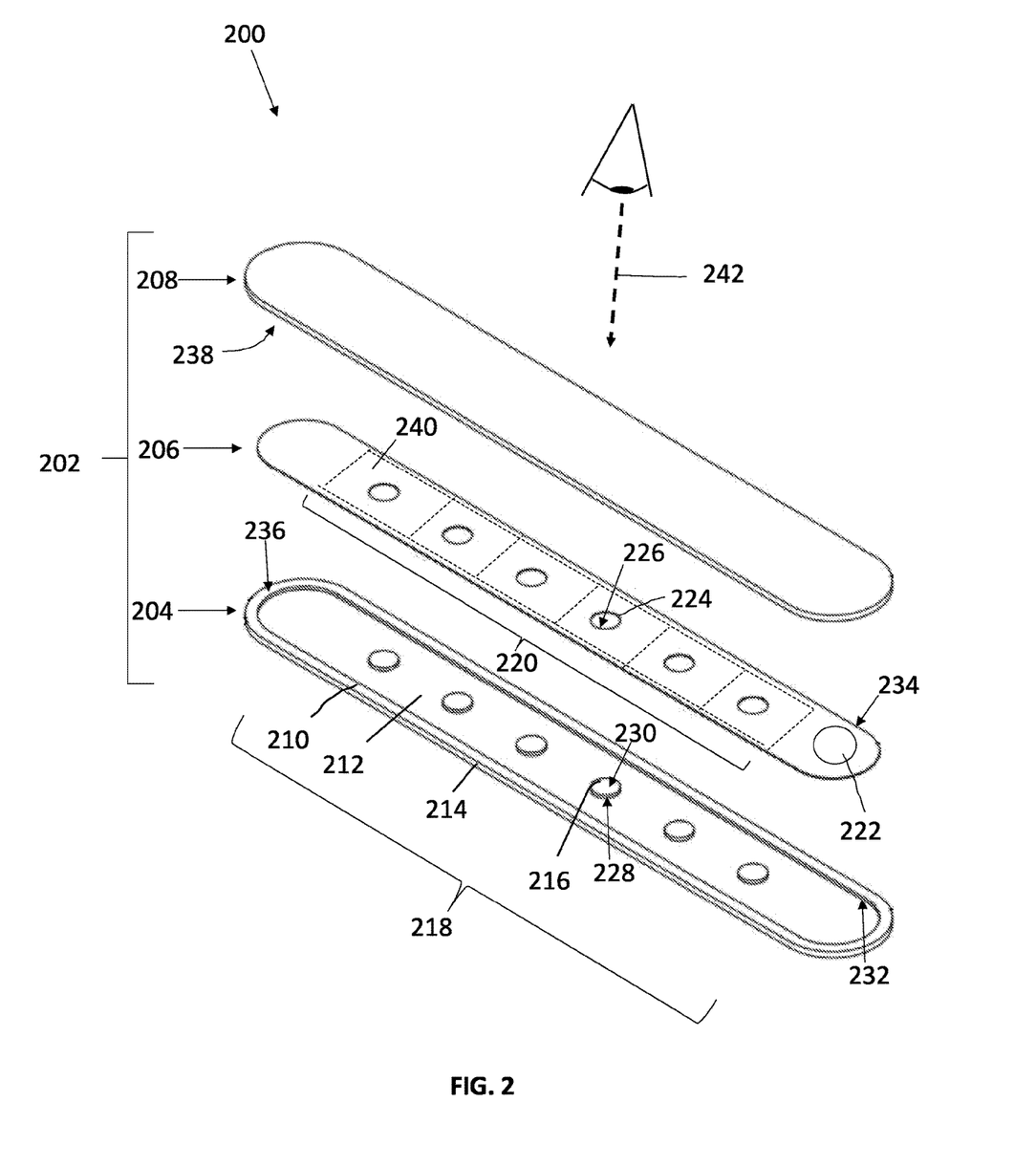
FIG. 2 depicts a blown-up view of an icterometer, according to some implementations of the description.

FIG. 2 depicts a blown-up view of an icterometer 200, according to some implementations. In this implementation, a plate 202 includes a back plate 204, a middle layer 206, and a cover plate 208.

The back plate 204 includes a lip 210 protruding from a surface 212 of the back plate 204, at outer edge 214. The back plate 204 also includes a series of transparent protrusions 216 in a center area 218. The protrusions 214 protrude away from surface 210, and in the same direction as the lip 208. In some implementations, the protrusions 214 protrude and equal amount or less than the lip 210.

The middle layer 206 includes a color gradient 220, and a series of through holes 224. In some implementations, the middle layer 206 also includes a lighting indicator 222. Each of the through holes 224 border a corresponding protrusion 216. For example, when assembled, the edges 226 of through hole 224, surround the edges 228 of transparent protrusion 216. The protrusions 216 are transparent through surface 230 and define the perimeter of windows through plate 202. A first surface 232 of lip 210 borders the edge 234 of the middle layer 206.

The cover plate 208 includes a transparent material, for example at least in areas covering color gradient 220 and lighting indicator 222. Accordingly, the cover plate provides a view of the color gradient 220 and lighting indicator 222. The cover plate 208 also provides viewing through the plate 202 at positions corresponding to the protrusions 216.

A second surface 236 of lip 210 contacts a surface 238 of the cover plate 208 providing a waterproof seal. In some implementations the surface 236 and surface 238 are flat. In some implementations the surface 236 and 238 are curved. In some implementations, the surface 236 includes a groove and the surface 238 includes a corresponding lip or protrusion that mates with the groove. In some implementations, the surface 238 includes a groove and the surface 236 includes a corresponding lip or protrusion. In some implementations, the surfaces 236 and 238 are in direct contact. In some implementations, the surface 236 are not indirect contact, for example, wherein a gasket or an adhesive layer couples the surfaces. In some implementations, the surface 236 is coupled to the surface 238 by fusion welding or ultrasonic welding.

In some implementations, the middle layer 206 is a thin film such as a plastic film or metal foil. In some implementations, the middle layer is a web material such as paper. The color gradient 220 can be painted, printed or etched on a surface 240 of the middle layer 206. The lighting indictor 222 can be painted, coated, printed or etched on surface 240. The color gradient 220 and lighting indicator 222 can also be provided as an adhesive patch adhered to surface 240.

A viewing direction is indicated by dashed arrow 242. The user can view the surface 240 and step gradient of colors 220, lighting indicator 222 through cover plate 208. The user can also view through cover plate 208 and protrusions 216 through plate 202.

In some implementations, an icterometer described herein comprises an optically variable security element. For example, the icterometer described herein comprises an optically variable security element at an end of the icterometer distal from the end comprising the lighting indicator. Optically-variable elements display different optical effects, such as depth, motion, or chromatic effects, under different observation or illumination conditions. In some implementations, the optically variable element is a logo.

In some implementations, the icterometer comprises an optically variable security element on surface 104 or 102 at an end of the icterometer distal from the end comprising the lighting indicator 112. In some implementations, the middle layer 206 contains an optically variable security element on surface 240, or opposite surface, at an end of the icterometer distal from the end comprising the lighting indicator 222.

In some implementations, an icterometer descried herein comprises an expiry or recommended replacement element. For example, the icterometer described herein comprises an expiry date at an end distal from the end comprising the lighting indicator and on the opposite surface of the security element. The expiry date can be printed, painted, or etched.

In some implementations, the icterometer comprises an expiry date on surface 104 or 102 at end of the icterometer distal from the end comprising the lighting indicator 112 and on the opposite surface of the security element. In some implementations, the middle later 206 contains an expiry date painted, printed, or etched on surface 240, or opposite surface, at an end of the icterometer distal from the end comprising the lighting indicator 222.

Figure 3A:
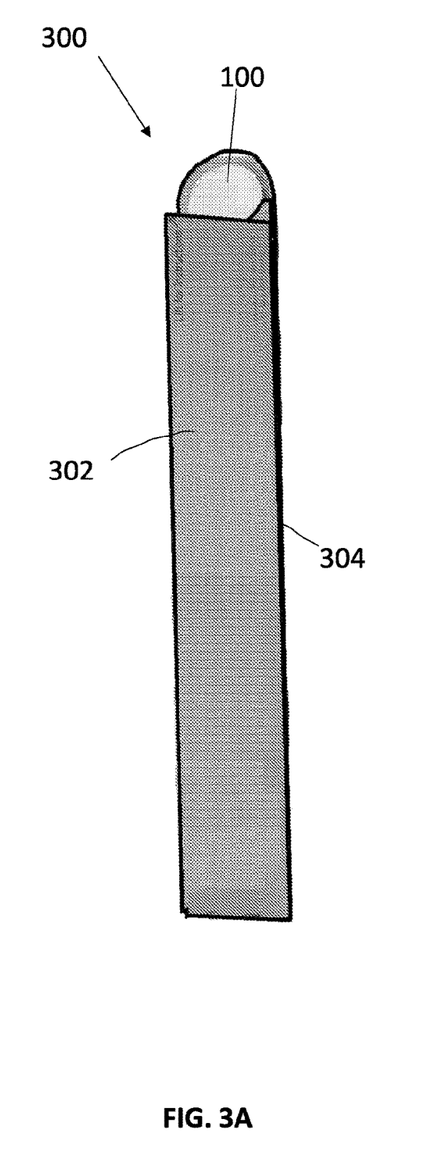
FIG. 3A depicts a kit including an icterometer, according to some implementations of the description.
Figure 3B:
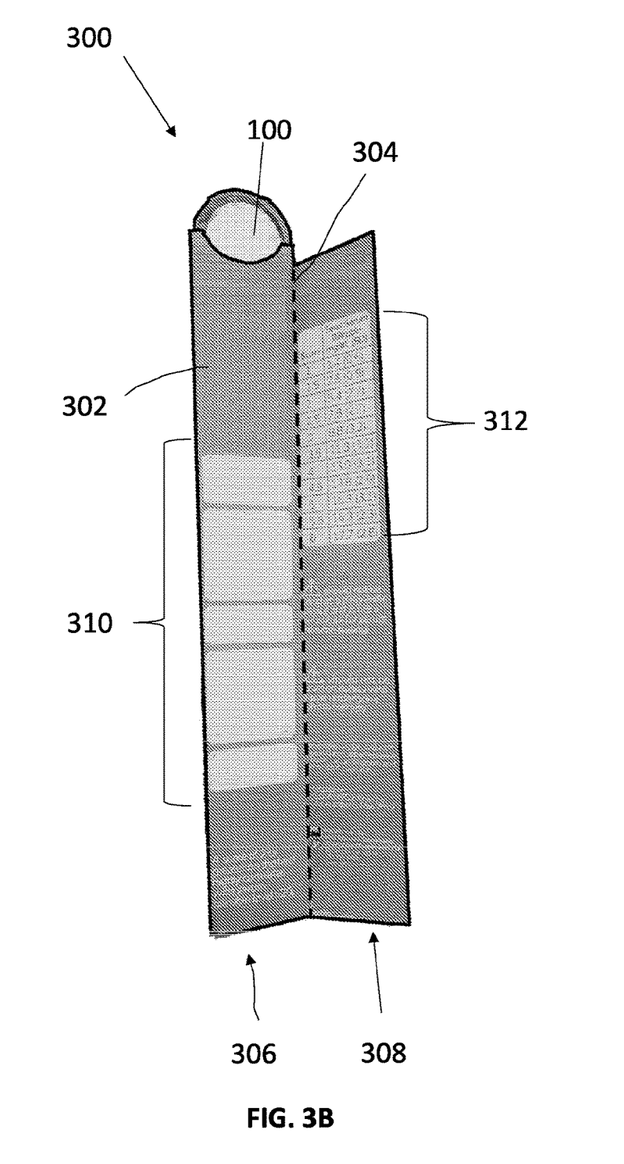
FIG. 3B depicts another view of the kit depicted in FIG. 3A.

According to some implementations of the description is a kit including an icterometer, such as icterometer 100 or 200, and a sleeve for holding the icterometer. FIG. 3A depicts a kit 300 having a sleeve 302 dimensioned for holding an icterometer 100 (or 200), according to some implementations. In some implementations, the kit 300 includes a hinge 304 in the sleeve 302. FIG. 3B depicts the sleeve 302 where the hinge 304 is indicated by a dashed line and is configured as a fold in the sleeve 302. The hinge 304 hingedly connects a first portions 306, and second portion 308 of the sleeve 302.

In some implementations, the first portion 306 and second portion 308 of the sleeve 302 comprise means for attaching a surface of the first portion 306 with a surface of the second portion 308. In some implementation, the means for attaching a surface of the first portion 306 with a surface of the second portion 308 includes a magnetic fastening assembly having a first and second magnetic elements. One of the first portion 306 and second portion 308 comprises the first magnetic element and the other of the first portion 306 and second portion 308 comprises the first magnetic element.

In some implementations, the sleeve 302 includes stepwise instructions 310 for operation of the icterometer. For example, instructions 310 can be printed on portion 306. In some implementations, the instructions can include cleaning instructions. In some implementations, the kit further includes cleaning agents, such as disinfectant wipes, in the sleeve or attached to the sleeve. In some implementations, the icterometer includes a table 312 listing colors or a color indicia and corresponding total serum bilirubin concentration. For example, the table 312 can be printed on portion 308. The table can list a "score" (corresponding to color indicia or fractions thereof) and the corresponding total serum bilirubin as shown in Table 1.

TABLE 1

Total Serum Bilirubin

| Score (color indicia) | Total Serum Bilirubin | |
|---|---|---|
| | mg/dL (SD) | μmol/L (SD) |
| 1 | 1.4 (0.6) | 24 (10) |
| 1.5 | 2.5 (0.9) | 43 (15) |
| 2 | 5.4 (2.7) | 92 (46) |
| 2.5 | 7.6 (2.7) | 130 (46) |
| 3 | 8.8 (3.2) | 150 (55) |
| 3.5 | 11.3 (3.1) | 193 (53) |
| 4 | 13.0 (3.1) | 222 (53) |
| 4.5 | 13.8 (2.6) | 236 (44) |
| 5 | 15.3 (2.3) | 262 (53) |
| 5.5 | 16.3 (2.3) | 279 (39) |
| 6 | 17.7 (2.8) | 303 (48) |

Figure 4:
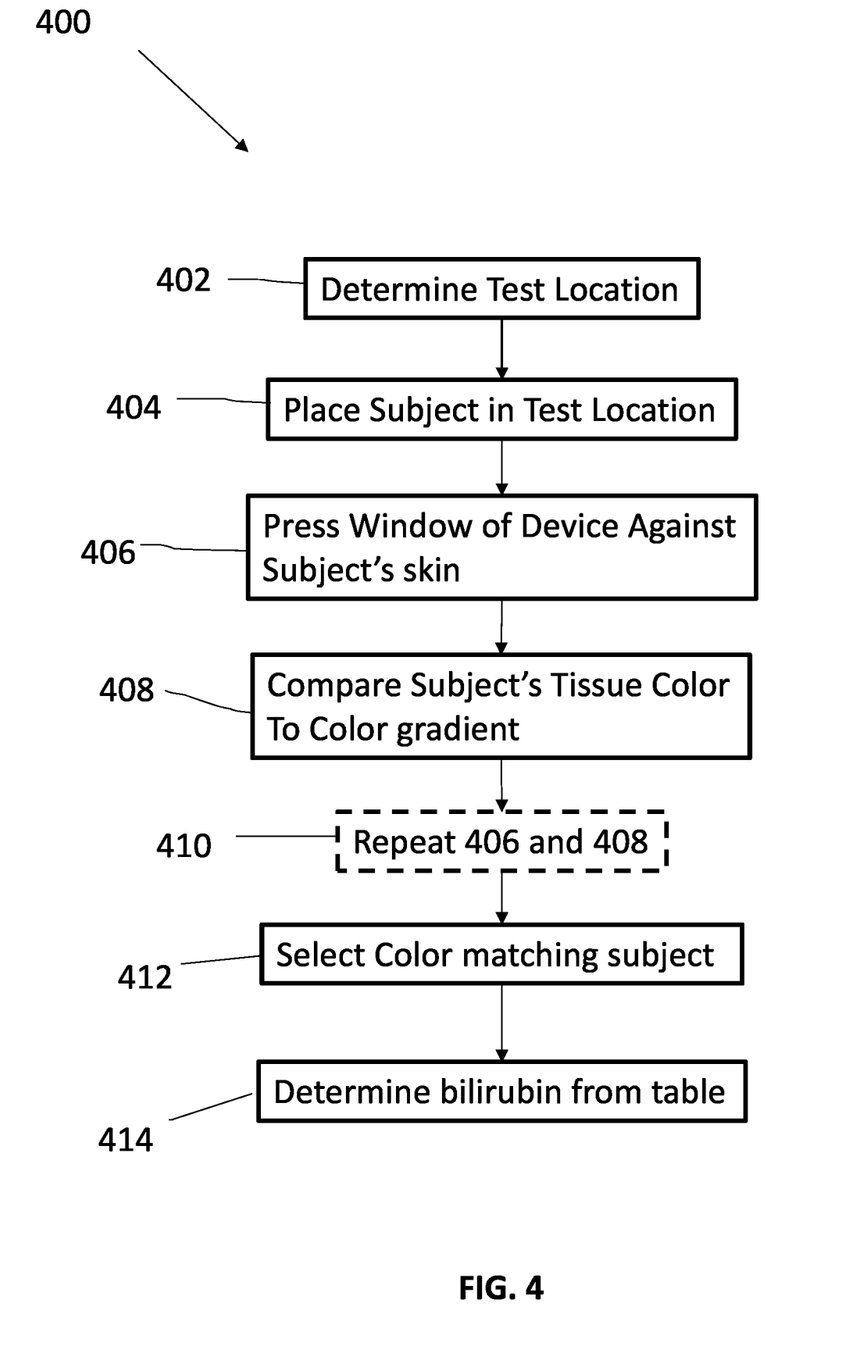
FIG. 4 is a flow diagram showing the steps for evaluating the total serum bilirubin concentration in a subject, according to some implementations.

FIG. 4 is a flow diagram 400 showing the steps for evaluating the total serum bilirubin concentration in a subject according to some implementations. The steps can be modified according to the icterometer being used. For example, in a first step 402, a test location is determined. The test location should be selected for appropriate lighting. For example, an appropriate location can include a place with daylight or natural daylight simulators. In some implementations, this can be done by selecting a location, such as a location next to a window during daylight hours, or a location having D50 or D65 illuminators. In implementations where the icterometer includes a lighting indicator the location can be confirmed to be appropriate by using the lighting indicator 112 (FIG. 1), or 222 (FIG. 2). Once the test location 402 is determined, the subject is placed 404 in the test location for subsequent testing.

Testing includes pressing a window, such as one window 110 (FIG. 1) against the subject's skin 406. Any exposed skin of the subject can be used. In some implementations, the nose is used. In other implementations, a knee is used. In other implementations, the sole of a foot can be used. The amount of pressure applied is enough to blanch the skin and thereby reveal the color of subcutaneous tissue. Testing also includes comparing the subcutaneous tissue color viewed through the window 110 to the color bordering the window 406 (e.g., color gradients 106 of FIG. 1). Optionally, the steps 406 and 408 are repeated in step 410. The repeated step 410 can be more than once, for example this can be repeated for each color in step wise color gradient 106.

The repeat step 410 is done enough times for the user to select 412 a color 106 that most closely matches the subcutaneous tissue color of the subject. In implementations where the icterometer includes a color indicium 114 (FIG. 1), the color indicia are noted. The color 106 or color indicia 114 is compared 414 to tabulated values of corresponding bilirubin levels, thereby determining the bilirubin level for the subject.

Although the devices described herein are icterometer, for example icterometer 100 (FIG. 1), other uses for the device are contemplated. The device can be used for any application where the tissue color needs to be determined. For example, the devices can be used for colorimetric assessment of skin color for skin grafting. As another example, the device can be used for the evaluation of anemia. The devices can also be used to determine a surface color. For example, in these implementations, the device is not pressed against the subject to reveal the subcutaneous tissue color, but simply placed against a surface such as the subject's skin or other surfaces. For example, the devices can be used for matching tooth enamel color to a series of shades use for dental prosthetics. For such applications, different gradient of colors that what is used for the icterometer 100 can be used. The device can even be used for surface color matching for inanimate objects, such as wall color.

Exemplary embodiments of the disclosure can be described by the following numbered embodiments:

Embodiment 1: An icterometer comprising: (a) a plate including a surface comprising, a step wise gradient of colors; (b) a series of windows in the surface, each window in the series bordered by one of the colors, and each window including a transparent portion in the plate; and (c) a lighting indicator configured to indicate the quality of lighting.

Embodiment 2: The icterometer according of embodiment 1, further comprising a corresponding color indicium for each color in the color gradient on the surface or on a transparent external surface overlapping the color gradients.

Embodiment 3: The icterometer according to embodiment 1 or 2, wherein the lighting indicator is a metameric pair of colored areas on the surface.

Embodiment 4: The icterometer according to any one of embodiments 1-3, wherein the metameric pair displays metamerism under natural daylight or natural daylight simulators.

Embodiment 5: The icterometer according to any one of embodiments 1-4, wherein the lighting is a D50 or a D65 lighting.

Embodiment 6: The icterometer according to any one of embodiments 1-5, wherein the plate is waterproof and inert to cleaning solutions applied to an external surface.

Embodiment 7: The icterometer according to any one of embodiments 1-6, wherein an external surface of the plate is coated with an antimicrobial coating.

Embodiment 8: The icterometer according to any one of embodiments 1-7, wherein the plate includes acrylic, polycarbonate, a silica-based glass, or combinations thereof.

Embodiment 9: The icterometer according to any one of embodiments 1-8, wherein the surface comprising a stepwise gradient of colors is encased in an interior of the plate.

Embodiment 10: The icterometer according to any one of embodiments 1-9, wherein the stepwise gradient of colors comprises at least 3 and not more than 10 colors.

Embodiment 11: The icterometer according to any one of embodiments 1-10, wherein the colors correspond to the colors of subcutaneous tissue of a subject having a total serum bilirubin between about 1.4 and 18 mg/dL.

Embodiment 12: The icterometer according to any one of embodiments 1-11, wherein the plate is configured as an elongated flat object having a length between about 10 cm and 40 cm, a width between about 2 cm and 5 cm, and a thickness of between about 1 mm and 5 mm.

Embodiment 13: The icterometer according to any one of embodiments 1-12, wherein the plate comprises: (a) a back plate including, a lip protruding from a surface of the back plate at an outer edge of the back plate, and a series of transparent protrusions in a center area and protruding in the same direction as the lip; (b) a middle layer including the color gradient, the lighting indicator, and a series of through holes, each through hole bordering each one of the transparent protrusions and defining one of the windows, and wherein a first surface of the lip borders an edge of the middle layer; (c) a cover plate comprising a transparent material for viewing of the color gradient and the lighting indicator, and for viewing through the plate at positions corresponding to the transparent protrusions on the back plate; and (d) wherein a second surface of the lip is coupled to a surface of the cover plate and provides a waterproof seal.

Embodiment 14: The icterometer according to any one of embodiments 1-13, wherein the second surface of the lip comprises an adhesive layer.

Embodiment 15: The icterometer according to any one of embodiments 1-14, wherein the middle layer comprises a web material and the color gradient and lighting indicator are printed, coated or otherwise attached to the web material.

Embodiment 16: An icterometer kit comprising: the icterometer according to any one of embodiments 1-15 or 21-28, and a sleeve dimensioned for holding the icterometer.

Embodiment 17: The icterometer kit according to embodiment 16, wherein the sleeve includes stepwise instruction for operation of the icterometer.

Embodiment 18: The icterometer kit according to any one of embodiments 16-17, wherein the sleeve includes a table listing colors and a corresponding total serum bilirubin concentration.

Embodiment 19: A method for evaluation of total serum bilirubin concentration in a subject comprising: (a) determining a test location having natural or simulated natural lighting using the lighting indicator of the icterometer of any one of claims 1 to 15; (b) placing the subject in the test location; (c) pressing a window of the icterometer against the subject's skin to blanch the skin and reveal a subcutaneous tissue color through the window; (d) comparing the subcutaneous tissue color viewed through the window to the color bordering the window; (e) repeating steps (c) and (d) using one or more additional windows of the icterometer; (f) selecting a color that most closely matches the subcutaneous tissue color of the subject; and (g) determining a bilirubin level from tabulated values of color and corresponding bilirubin concentration.

Embodiment 20: The method for evaluation of bilirubin in a subject according to embodiment 19, wherein: (a) the icterometer includes at least a first window and a second window; (b) the subcutaneous tissue color corresponds to a color between a first color indicated through the first window and a second color indicated through the second window; and (c) the corresponding bilirubin level is a selected value between the bilirubin level associated with the color viewed through the first window and the second window.

Embodiment 21: An icterometer comprising: (a) a plate including a surface comprising, a stepwise gradient of colors; (b) a series of windows in the surface, each window in the series bordered by one of the colors, and each window including a transparent portion in the plate; and (c) wherein the plate is waterproof and inert to cleaning solutions applied to an external surface.

Embodiment 22: The icterometer according to any one of embodiments 1-15 or 21, wherein an external surface of the plate is coated with an antimicrobial coating.

Embodiment 23: The icterometer according to any one of embodiments 1-15 or 21-22, wherein the plate includes acrylic, polycarbonate, a silica-based glass, or combinations thereof.

Embodiment 24: The icterometer according to any one of embodiments 1-15 or 21-23, wherein the surface comprising a stepwise gradient of colors is encased in an interior of the plate.

Embodiment 25: The icterometer according to any one of embodiments 1-15 or 21-24, wherein the plate is configured as an elongated flat object having a length between about 10 cm and 40 cm, a width between about 2 cm and 5 cm, and a thickness of between about 1 mm and 5 mm.

Embodiment 26: The icterometer according to any one of embodiments 1-25, wherein the plate comprises: (a) a back plate including, a lip protruding from a surface of the back plate at an outer edge of the back plate, and a series of transparent protrusions in a center area and protruding in the same direction as the lip; (b) a middle layer including the color gradient, and a series of through holes, each through hole bordering each one of the transparent protrusions and defining one of the windows, and wherein a first surface of the lip borders an edge of the middle layer; (c) a cover plate comprising a transparent material for viewing of the color gradient, and for viewing through the plate at positions corresponding to the transparent protrusions on the back plate; and (d) wherein a second surface of the lip is coupled to a surface of the cover plate and provides a waterproof seal.

Embodiment 27: The icterometer according to embodiment 26, wherein the second surface of the lip comprises an adhesive layer.

Embodiment 28: The icterometer according to any one of embodiments 26-27, wherein the middle layer comprises a web material and the color gradient is printed, coated or otherwise attached to the web material.

Embodiment 29: A method for evaluation of total serum bilirubin concentration in a subject comprising: (a) identifying a test location having natural or simulated natural lighting; (b) placing the subject in the test location; (c) pressing a window of the icterometer according to any one of paragraphs 1-15 or 20-28, against the subject's skin to blanch the skin and reveal a subcutaneous tissue color through the window; (d) comparing the subcutaneous tissue color viewed through the window to the color bordering the window; (e) repeating steps (c) and (d) using one or more additional windows of the icterometer; (f) selecting a color that most closely matches the subcutaneous tissue color of the subject; and (g) determining a bilirubin level from tabulated values of color and corresponding bilirubin concentration.

Embodiment 30: The method for evaluation of bilirubin in a subject according to embodiment 29, wherein: (a) the icterometer includes at least a first window and a second window; (b) the subcutaneous tissue color corresponds to a color between a first color indicated through the first window and a second color indicated through the second window; and (c) the corresponding bilirubin level is a selected value between the bilirubin level associated with the color viewed through the first window and the second window.

Some additional Exemplary embodiments of the disclosure can be described by the following numbered embodiments:

Embodiment 1: An icterometer comprising: (a) a plate including a surface comprising, a step wise gradient of colors; and (b) a series of windows in the surface, each window in the series bordered by one of the colors, and each window including a transparent portion in the plate, and wherein: (i) the icterometer comprises a lighting indicator configured to indicate the quality of lighting; and/or (ii) the plate is waterproof and inert to cleaning solutions applied to an external surface.

Embodiment 2: The icterometer according to claim 1, further comprising a corresponding color indicium for each color in the color gradient on the surface or on a transparent external surface overlapping the color gradients.

Embodiment 3: The icterometer according to claim 1 or 2, wherein the icterometer comprises a lighting indicator configured to indicate the quality of lighting.

Embodiment 4: The icterometer according to claim 3, wherein the lighting indicator is a metameric pair of colored areas on the surface.

Embodiment 5: The icterometer according to claim 4, wherein the metameric pair displays metamerism under natural daylight or natural daylight simulators.

Embodiment 6: The icterometer according to according to claim 4, wherein the metameric pair displays metamerism under D50 or D65 lighting.

Embodiment 7: The icterometer according to any one of claims 1-6, wherein the plate is waterproof and inert to cleaning solutions applied to an external surface.

Embodiment 8: The icterometer according to any one of claims 1-7, wherein an external surface of the plate is coated with an antimicrobial coating.

Embodiment 9: The icterometer according to any one of claims 1-8, wherein the plate includes acrylic, polycarbonate, a silica-based glass, or combinations thereof.

Embodiment 10: The icterometer according to any one of claims 1-9, wherein the surface comprising a stepwise gradient of colors is encased in an interior of the plate.

Embodiment 11: The icterometer according to any one of claims 1-10, wherein the stepwise gradient of colors comprises at least 3 and not more than 10 colors.

Embodiment 12: The icterometer according to any one of claims 1-11, wherein the colors correspond to the colors of subcutaneous tissue of a subject having a total serum bilirubin between about 1.4 and 18 mg/dL or between 24 and 303 μmon.

Embodiment 13: The icterometer according to any one of claims 1-12, wherein the plate is configured as an elongated flat object having a length between about 10 cm and 40 cm, a width between about 2 cm and 5 cm, and a thickness of between about 1 mm and 5 mm.

Embodiment 14: The icterometer according to any one of claims 1-13, wherein the plate comprises: (a) a back plate including, a lip protruding from a surface of the back plate at an outer edge of the back plate, and a series of transparent protrusions in a center area and protruding in the same direction as the lip; (b) a middle layer including the color gradient, the lighting indicator, and a series of through holes, each through hole bordering each one of the transparent protrusions and defining one of the windows, and wherein a first surface of the lip borders an edge of the middle layer; and (c) a cover plate comprising a transparent material for viewing of the color gradient and the lighting indicator, and for viewing through the plate at positions corresponding to the transparent protrusions on the back plate, and wherein a second surface of the lip is coupled to a surface of the cover plate and provides a waterproof seal.

Embodiment 15: The icterometer according to claim 14, wherein the second surface of the lip comprises an adhesive layer.

Embodiment 16: The icterometer according to claim 14 or 15, wherein the middle layer comprises a web material and the color gradient and lighting indicator are printed, coated or otherwise attached to the web material.

Embodiment 17: The icterometer according to any one of claims 1-16, wherein the icterometer comprises an optically variable security element.

Embodiment 18: The icterometer according to any one of claims 1-17, wherein the icterometer comprises an expiry or recommended replacement element.

Embodiment 19: An icterometer kit comprising: the icterometer according to any one of claims 1-18 and a sleeve dimensioned for holding the icterometer.

Embodiment 20: The icterometer kit according to claim 19, wherein the sleeve includes stepwise instruction for operation of the icterometer.

Embodiment 21: The icterometer kit according to claim 19 or 20, wherein the sleeve includes a table listing colors and a corresponding total serum bilirubin concentration.

Embodiment 22: A method for evaluation of total serum bilirubin concentration in a subject comprising: (a) determining a test location having natural or simulated natural lighting using the lighting indicator of the icterometer of any one of claims 1 to 17; (b) placing the subject in the test location; (c) pressing a window of the icterometer against the subject's skin to blanch the skin and reveal a subcutaneous tissue color through the window; (d) comparing the subcutaneous tissue color viewed through the window to the color bordering the window; (e) repeating steps (c) and (d) using one or more additional windows of the icterometer; (f) selecting a color that most closely matches the subcutaneous tissue color of the subject; and (g) determining a bilirubin level from tabulated values of color and corresponding bilirubin concentration.

Embodiment 23: The method for evaluation of bilirubin in a subject according to claim 22, wherein: the icterometer includes at least a first window and a second window; the subcutaneous tissue color corresponds to a color between a first color indicated through the first window and a second color indicated through the second window; and the corresponding bilirubin level is a selected value between the bilirubin level associated with the color viewed through the first window and the second window.

Some Selected Definitions

The terminology used herein is for the purpose of describing particular embodiments only and is not intended to be limiting of the invention. As used herein, the singular forms "a," "an," and "the" are intended to include the plural forms as well, unless the context clearly indicates otherwise. Furthermore, to the extent that the terms "including," "includes," "having," "has," "with," or variants thereof, are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art. Furthermore, terms, such as those defined in commonly used dictionaries, should be interpreted as having a meaning that is consistent with their meaning in the context of the relevant art, and will not be interpreted in an idealized or overly formal sense unless expressly so defined herein.

While various embodiments of the present invention have been described above, it should be understood that they have been presented by way of example only, and not limitation. Numerous changes to the disclosed embodiments can be made in accordance with the disclosure herein, without departing from the spirit or scope of the invention. Thus, the breadth and scope of the present invention should not be limited by any of the above-described embodiments. Rather, the scope of the invention should be defined in accordance with the following claims and their equivalents.

The embodiments will be more readily understood by reference to the following examples, which are included merely for purposes of illustration of certain aspects and embodiments of the present invention and should not be construed as limiting. As such, it will be readily apparent that any of the disclosed specific constructs and experimental plan can be substituted within the scope of the present disclosure.

Examples

Exemplary Ruler Icterometer

Figure 5:
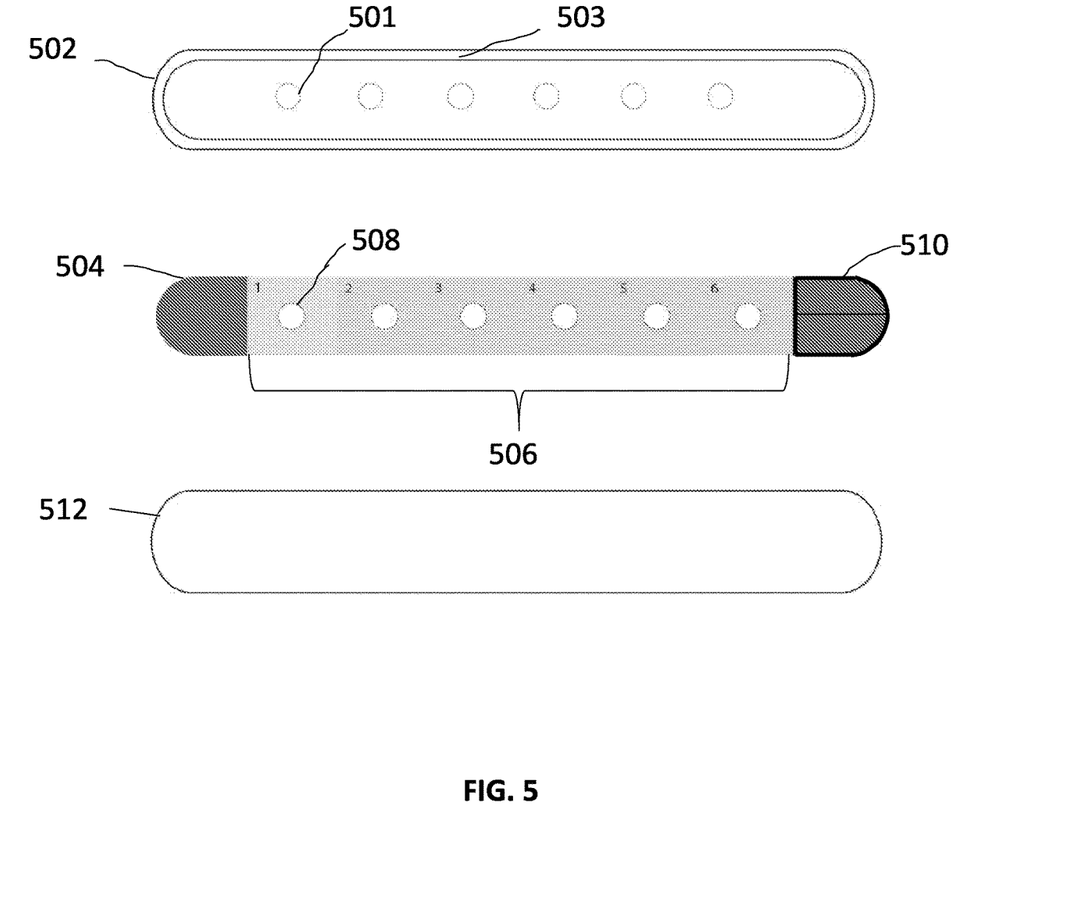
FIG. 5 depicts an embodiment of an icterometer, according to some implementations of the description.

An exemplary icterometer includes the following components as shown by FIG. 5:
 i. A back plate 502 which is machined 1/16" acrylic for paper clearance. Areas 501 (protrusions) and 503 (lip) are not machined.
 ii. Paper 504 which is a printed and cut paper insert 0.001" thick. Paper has a step gradient of colors 506 and holes 508 as well as PANTONE® D50 or D65 lighting indicator 510.
 iii. A front plate 512. Machined 1/16" or 0.04" thick acrylic. The length is 7.25" and ends have 0.5" radius curvature.

Assembly

The three components (i, ii, and iii) above are layered together, with the paper in the middle layer. These are permanently fixed. The fixing points should be the outer edges of the ruler where the two plates meet. There should be no attachment in the hole areas. A sleeve for holding the icterometer is cut, printed and assembled. The ruler is placed in the sleeve.

Although the invention has been illustrated and described with respect to one or more implementations, equivalent alterations, and modifications will occur or be known to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. An icterometer comprising:
 a plate including a surface comprising:
  a step wise gradient of colors;
  a series of windows in the surface, each window in the series bordered by one of the colors, and each window including a transparent portion in the plate, and
 wherein the plate comprises:
  a back plate including, a lip protruding from a surface of the back plate at an outer edge of the back plate, and a series of transparent protrusions in a center area and protruding in the same direction as the lip;
  a middle layer including the color gradient, the lighting indicator, and a series of through holes, each through hole bordering each one of the transparent protrusions and defining one of the windows, and wherein a first surface of the lip borders an edge of the middle layer;
  a cover plate comprising a transparent material for viewing of the color gradient and the lighting indicator, and for viewing through the plate at positions corresponding to the transparent protrusions on the back plate; and
  wherein a second surface of the lip is coupled to a surface of the cover plate and provides a waterproof seal;
 and
 wherein:
  (i) the icterometer comprises a lighting indicator configured to indicate the quality of lighting; and/or
  (ii) the plate is waterproof and inert to cleaning solutions applied to an external surface.

2. The icterometer according to claim 1, wherein the second surface of the lip comprises an adhesive layer.

3. The icterometer according to claim 1, wherein the middle layer comprises a web material and the color gradient and lighting indicator are printed, coated or otherwise attached to the web material.

4. The icterometer according to claim 1, further comprising a corresponding color indicium for each color in the color gradient on the surface or on a transparent external surface overlapping the color gradients.

5. The icterometer according to claim 1, further wherein the icterometer comprises a lighting indicator configured to indicate the quality of lighting.

6. The icterometer according to claim 5, wherein the lighting indicator is a metameric pair of colored areas on the surface.

7. The icterometer according to claim 6, wherein the metameric pair displays metamerism under natural daylight or natural daylight simulators.

8. The icterometer according to according to claim 6, wherein the metameric pair displays metamerism under D50 or D65 lighting.

9. The icterometer according to claim 1, further wherein the plate is waterproof and inert to cleaning solutions applied to an external surface.

10. The icterometer according to claim 1, further wherein an external surface of the plate is coated with an antimicrobial coating.

11. The icterometer according to claim 1, further wherein the plate includes acrylic, polycarbonate, a silica-based glass, or combinations thereof.

12. The icterometer according to claim 1, further wherein the surface comprising a stepwise gradient of colors is encased in an interior of the plate.

13. The icterometer according to claim 1, further wherein the stepwise gradient of colors comprises at least 3 and not more than 10 colors.

14. The icterometer according to claim 1, further wherein the colors correspond to the colors of subcutaneous tissue of a subject having a total serum bilirubin between about 1.4 and 18 mg/dL or between 24 and 303 μmol/L.

15. The icterometer according to claim 1, further wherein the plate is configured as an elongated flat object having a length between about 10 cm and 40 cm, a width between about 2 cm and 5 cm, and a thickness of between about 1 mm and 5 mm.

16. An icterometer kit comprising: the icterometer according to claim 1 and a sleeve dimensioned for holding the icterometer.

17. The icterometer kit according to claim 16, wherein the sleeve includes stepwise instruction for operation of the icterometer.

18. The icterometer kit according to claim 16, wherein the sleeve includes a table listing colors and a corresponding total serum bilirubin concentration.

19. A method of using the icterometer of claim 1 for evaluation of total serum bilirubin concentration in a subject comprising:
(a) determining a test location having natural or simulated natural lighting using the lighting indicator of the icterometer of claim 1;
(b) placing the subject in the test location;
(c) pressing a window of the icterometer against the subject's skin to blanch the skin and reveal a subcutaneous tissue color through the window;
(d) comparing the subcutaneous tissue color viewed through the window to the color bordering the window;
(e) repeating steps (c) and (d) using one or more additional windows of the icterometer;
(f) selecting a color that most closely matches the subcutaneous tissue color of the subject; and
(g) determining a bilirubin level from tabulated values of color and corresponding bilirubin concentration.

20. The method of claim 19, wherein:
the subcutaneous tissue color corresponds to a color between a first color indicated through a first window and a second color indicated through a second window; and
the corresponding bilirubin level is a selected value between the bilirubin level associated with the color viewed through the first window and the second window.

\* \* \* \* \*